(12) United States Patent
Eigemann et al.

(10) Patent No.: US 7,284,474 B2
(45) Date of Patent: Oct. 23, 2007

(54) PISTON-PUMPING SYSTEM HAVING O-RING SEAL PROPERTIES

(75) Inventors: Jutta Eigemann, Dortmund (DE); Johannes Geser, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 267 days.

(21) Appl. No.: 10/727,286

(22) Filed: Dec. 3, 2003

(65) Prior Publication Data

US 2004/0134495 A1 Jul. 15, 2004

Related U.S. Application Data

(60) Provisional application No. 60/431,640, filed on Dec. 6, 2002.

(30) Foreign Application Priority Data

Dec. 6, 2002 (EP) .................................. 02027243

(51) Int. Cl.
*F16J 15/18* (2006.01)
(52) U.S. Cl. .................. 92/168; 417/416; 604/151; 604/152
(58) Field of Classification Search ........... 604/131, 604/134, 135, 151, 152; 277/438, 910; 92/168; 417/416
See application file for complete search history.

(56) References Cited

U.S. PATENT DOCUMENTS

| 4,246,833 | A | | 1/1981 | Burklund |
| 4,468,221 | A | * | 8/1984 | Mayfield .................... 604/152 |
| 4,813,932 | A | * | 3/1989 | Hobbs .......................... 604/74 |
| 4,961,726 | A | * | 10/1990 | Richter ........................ 604/74 |
| 6,132,755 | A | | 10/2000 | Eicher et al. |
| 6,389,955 | B1 | | 5/2002 | Schaefer |
| 6,409,175 | B1 | * | 6/2002 | Evans et al. ................. 277/314 |
| 6,547,756 | B1 | * | 4/2003 | Greter et al. ................. 604/74 |
| 6,916,159 | B2 | * | 7/2005 | Rush et al. .................. 417/321 |

FOREIGN PATENT DOCUMENTS

| DE | 19921951 A1 | 11/1999 |
| EP | 0361260 A2 | 4/1990 |

* cited by examiner

*Primary Examiner*—Kevin C. Sirmons
*Assistant Examiner*—Laura C. Schell
(74) *Attorney, Agent, or Firm*—Michael P. Morris; Mary-Ellen M. Devlin; Alan R. Stempel

(57) ABSTRACT

The present invention relates to a piston pumping system for substantially gas-free measurement and/or pumping of predetermined quantities of liquids, preferably pharmaceutical liquids containing oxidation-prone ingredients. Preferably, the system is used as a micropump or as a component thereof in medical devices such as transdermal therapeutic systems, for example.

17 Claims, 3 Drawing Sheets

PISTON-PUMPING SYSTEM HAVING O-RING SEAL PROPERTIES

RELATED APPLICATIONS

Benefit of U.S. Provisional Application No. 60/431,640, filed Dec. 6, 2002 is herby claimed.

FIELD OF THE INVENTION

The present invention relates to a piston pumping system for substantially gas-free measurement and/or pumping of predetermined quantities of liquids, preferably pharmaceutical liquids containing oxidation-prone ingredients. Preferably, the system is used as a mini- or micropump or as a component thereof in medical devices such as for example transdermal therapeutic systems.

PRIOR ART

In medical devices for delivering pharmaceutical liquids it is often necessary to measure defined volumes of the liquid from a storage system using a pumping system and transfer them to the place of delivery. The smaller and handier the device, the smaller the pump must be. In conventional filling systems and/or pump-operated transporting systems it may happen that the liquid comes into contact with gas from the environment or this gas mixes with the liquid during the transfer from one space into another by means of the pump. This intermingling of gas and liquid is not always desirable. In some cases this effect is unacceptable. Thus, for example, there are liquids containing substances prone to oxidation and mixing with oxygen from the air, for example, critically affects the pharmaceutical quality of the formulation. In other cases the gas which has entered the measuring chamber can falsify the measuring process and thus alter the quantity of liquid to be delivered. In other cases in which the liquid is administered parenterally, e.g. intravenously, the liquid to be delivered must not of itself contain any appreciable amounts of gas, so as not to endanger the health of the patient.

This problem of gas penetration occurs particularly with piston pumping systems in which the liquid to be taken from a storage system is transferred into a measuring chamber by means of a cyclically reciprocating piston and from there is delivered to the intended location. In systems of this kind the pump piston moves within a guide tube and is sealed off from it. The seal is intended to prevent any liquid from escaping from the filling chamber or any gas from entering the filling chamber.

Examples of medical devices suitable for the invention include transdermal therapeutic systems as disclosed in EP 0840634. Such systems consist essentially of a reservoir for the medicament and at least one—typically several—micropins with capillary openings which are connected to the reservoir so that the pharmaceutical composition in the form of a solution containing an active substance travels from the reservoir into the micro-pins. When the transcorneal system is placed on the skin the pins pass through the stratum corneum and possibly the epidermis so that the pharmaceutical composition gains direct access to the innervated layer of the skin. In this way the pharmaceutical composition can flow from the reservoir through the capillary openings of the micro-pins into vascularised parts of the skin in order to be absorbed from there into the blood stream through the capillary system. In the systems the active substance is usually in the form of a solution to ensure satisfactory transportation through the capillary openings of the micropins of the transcorneal system.

The medicament may be transported "actively"—e.g. by means of excess pressure stored in the reservoir or by electrostatic or capillary forces, or using a pump integrated in the system. An active system of this kind is described in EP 0840634 B1.

DESCRIPTION OF THE INVENTION

The aim of the present invention is to provide a piston-operated pumping system which guarantees that during the measuring and/or pumping of liquids by means of a piston pumping system, substantially no gas can pass along the piston from outside and enter the filling or pumping chamber.

A further objective is to provide a pumping system for medical devices which prevents the pharmaceutical liquid from being mixed with oxygen, air or any other gas as a result of the measuring or pumping process.

A further objective is to overcome the disadvantages of pumping systems in medical devices known from the prior art.

DETAILED DESCRIPTION OF THE INVENTION

The present invention now relates to a piston pumping system which can be used as or in a small pump, e.g. a mini- or micropump, in medical devices for the direct administration of pharmaceutical formulations. Preferably, the device according to the invention is used in medical devices which require or may require a pump for delivering liquids. However, the invention may be used in any other piston pumping system, not restricted to medical devices, in which it is of advantage. The invention is also not restricted to mini-pumps or micropumps but may also be applied to larger pumping systems.

Within the scope of the present invention, the term medical device preferably denotes application devices for liquids such as transdermal therapeutic systems with active transportation of the active substance, devices for the intravenous administration of liquid formulations in small amounts, atomisers for liquids such as inhalers, particularly propellant-free inhalers, needleless injectors, eye sprays, etc. Medical devices of this kind also serve to some extent as primary packaging for pharmaceutical preparations or may be regarded as such, as the pharmaceutical preparation is initially stored in these devices before the device is used on or for the patient. Therefore, the concept also includes medical devices which serve as primary packaging.

According to the invention, a piston pumping system is provided which, using sealing materials suitable for food or drug use, improves the sealing of the piston in the pumping system against the diffusion of air or other gases from the outer environment into the liquid which is to be drawn up or measured and thus reduces the penetration of air or other gases into this liquid. The pumping system according to the invention overcomes the above mentioned disadvantages of current pumping systems.

A pumping and measuring system suitable for the invention may consist of a chamber having a liquid inlet and a liquid outlet, a piston being connected to the chamber in such a way that by a stroke-like movement of the piston along its longitudinal axis liquid can be taken in from a storage system in a predetermined quantity through the liquid inlet and from there can be delivered, optionally under pressure, through the liquid outlet.

Between two stroke movements the system can rest. In many cases the storage system is constructed as a flexible container which collapses as liquid is removed. In storage systems of this kind, particularly systems with very small dimensions, i.e. a measuring or pumping chamber with a capacity in the microliter range and corresponding cross sections for the inlets and outlets and a storage system, a static underpressure or static vacuum may be produced in the chamber in the resting phase. This means that the underpressure in the storage system is passed on to the pumping chamber.

The pumping system according to the invention is therefore designed both for dynamic high pressure loading and also for dynamic and/or static underpressure loading. By high pressure is meant pressures of more than 1 bar. The system is preferably designed for a pressure of up to 600 bar, more preferably up to 250 bar. This pressure may be maintained for up to about 10 seconds, preferably up to 5 seconds, more preferably up to 2 seconds.

By underpressure is meant a pressure difference of preferably less than 0.5 bar, preferably less than 100 mbar and most preferably less than 50 mbar. By a static underpressure is meant that this is maintained for a period of more than 5 minutes, preferably more than 1 hour, more preferably more than 10 hours and most preferably about 24 hours.

Within the scope of the present invention the above mentioned chamber is also referred to as a pumping chamber or measuring chamber. Preferably, the chamber has a fill volume of from 1 microliter to 1 ml, more preferably from 1 microliter to 500 microliters, most preferably from 5 microliters to 100 microliters. Volumes of 5 microliters to 30 microliters are most preferred.

The liquid inlet or the supply system connected to the liquid inlet, which brings the liquid from the storage system into the chamber, is preferably formed by pipes or tubes. The cross section of the tube opening is preferably less than 1 mm, more preferably less than 0.5 mm.

The supply system preferably has a non-return valve which prevents the liquid sucked in from running back into the storage container. The system comprising the liquid inlet and/or the supply system is also referred to as the intake system within the scope of the present description of the invention.

The intake system may optionally be integrated in the pump piston. In this case the pump piston is a hollow piston. The hollow interior of the piston then constitutes the feed for the liquid from the storage system into the chamber or is connected to such a feed. In this case the intake system contains a non-return valve, preferably as an integral part of the piston.

The liquid outlet or the release system for the liquid connected to the liquid outlet, which supplies the liquid from the pumping or measuring chamber to its intended destination, may have a non-return valve of this kind, but this is not essential. The liquid outlet will always have a non-return valve when the filling system is such that it is possible or undesirable for the liquid forced out of the measuring chamber to flow back from the destination through the liquid outlet and back into the pumping or measuring chamber.

The situation is comparable when there is a danger of air being drawn into the pumping chamber from outside through the release system. Here again a non-return valve is advisable.

The system of fluid inlet and/or the above-mentioned release system is also referred to as the release system within the scope of the present description.

The moveable piston projecting into the pumping or measuring chamber is guided within a cylindrical bore of a solid element, for example a block or a wall. A block or a wall of this kind may be an independent element in the pumping system or may be an integral part of the chamber. The piston may be inserted into the chamber or extracted from it by means of a predetermined stroke movement. This stroke movement fills and empties the chamber. The dimensions of the piston and the chamber should be matched to each other accordingly.

The piston preferably has a length of 5 mm to 10 cm, preferably from 1 cm to 7.5 cm. The diameter of the piston is preferably 0.25 to 4 mm, more preferably 0.5 to 3 mm and most preferably 0.75 to 2.25 mm.

The stroke movement of the piston along its longitudinal axis preferably covers a length of from 1 mm to 5 cm, particularly from 0.25 cm to 3 cm. Stroke movements of from 0.5 cm to 2 cm are most preferred.

A seal on the piston seals off the space between the piston and the chamber, independently of the movement of the piston, thus preventing liquid from escaping. In other words the piston is guided within the pumping system such that in normal operation it cannot escape from the cylindrical guide and always performs its sealing function. The sealing materials, like all other materials of systems for dosing pharmaceutical liquids, are subject to particular requirements. Thus, they may be of such a nature that there is no impairment of the pharmaceutical quality of the liquid and no contamination which could endanger the health of the end consumer. These requirements apply particularly to the sealing material as well, which is generally an elastic polymer, from which constituents can continue to escape during use, which are undesirable in the liquids being dosed, for the reasons stated above. In connection with this the public discussion regarding plasticisers etc in packaging materials for foodstuffs and the like might be borne in mind. Therefore, within the scope of the pump according to the invention, the sealing systems used for the piston must be selected primarily so that they do not affect the quality of the liquid. The outline conditions relating to function must be subordinate to this criterion. Such secondary properties of the sealing material include the density of the material and/or its permeation coefficient for air or other gases.

According to the invention, the guiding of the piston within the pumping system is preferably effected by means of silicon seals as silicon has the properties which make it acceptable for use with food or pharmaceuticals as referred to above. One disadvantage of this sealing material and other sealing materials which are suitable under food or drug regulations is the fact that these materials have a relatively high permeation coefficient for air, with the result that air and oxygen can diffuse through the sealing material into the liquid being dispensed. Current sealing materials such as NBR or PU, for example, cannot be used in every case for pharmaceutical reasons.

Preferably the seal is in the form of an O-ring seal. By an O-ring is meant an annular seal, irrespective of the shape of its cross section. O-ring seals with a circular cross section are preferred.

The piston may be sealed off by one or more O-rings. Preferably there is at least one seal in the guide tube for the piston close to the point of entry of the piston into the pumping chamber.

When O-rings of this kind are incorporated for sealing dynamically loaded piston rods the prior art envisages cross sectional compression of 10% to about 15%. This is intended to provide a balanced ratio of wear to leaktightness.

Surprisingly, it has now been found that this installation ratio in the medical devices according to the invention does not provide a sufficient seal for static vacuum sealing. For seals of this kind compressions of more than 50% and a groove filling level of usually 80% or up to 100% in the case of vacuum seals are taught (Wilhelm Schmitt, "Kunststoffe und Elastomere in der Dichtungstechnik", W. Kohlhammer GmbH 1987, Chapter 2.1.4, page 228, Chapter 2.2.1, page 231). In the case of static vacuum seals, according to the prior art cited, compression levels of more than 50%, the use of vacuum grease, a peak-to-valley height of the groove and surrounding area of less than 0.5 microns and a very low gas permeability are essential prerequisites. The following O-ring basic elastomers are known, for ensuring low gas permeability:

Butyl rubber, epichlorohydrin, fluorocarbon rubber and nitrile rubber with a high acrylonitrile content.

Silicon rubbers are regarded as totally unsuitable as they have particularly high gas permeabilities.

The following table gives an overview of the gas permeabilities of different substances. The gas permeation is compared by means of the gas permeation coefficient P $[N*cm^3*mm/(m^2*h*bar)]$ for nitrogen ($N_2$):

|  | P at 20° C. | P at 80° C. |
|---|---|---|
| Butyl | 0.2-0.6 | 8-15 |
| Epichlorohydrin Copolymer | 0.5-4 | 10-40 |
| Epichlorohydrin Homopolymer | 0.04 | 1-5 |
| Fluorocarbon | 0.2-2 | 12-48 |
| Nitrile | 0.5-5 | 15-100 |
| Ethylene-Propylene | 2-10 | 40-100 |
| Polytetrafluoroethylene | 1.5-5 | 5-30 |
| Polyurethane | 0.5-1.3 | 18-50 |
| Silicon | 100-500 | 500-1200 |

However, such high compression leads to unacceptable wear and very high frictional forces under dynamic loading. The wear not only jeopardises the function according to the invention, in the long term, but may also result in contamination of the liquid in the pumping chamber and hence the active substance formulation with abraded particles, which is unacceptable from a pharmaceutical point of view.

Surprisingly, it has now been found that, contrary to the assumptions from the prior art, the problem of inadequate sealing of the O-ring seal against permeation or diffusion in static vacuum seals using seals with a gas permeation coefficient of 100 to 500 $N*cm^3*mm/(m^2*h*bar)$ can be solved without either increasing the compression of the seal or degreasing the seal but solely by adjusting the level of filling of the seal in the groove which holds it (groove filling level) to the optimum.

According to the invention the O-ring seal is subjected to a radial and possibly axial compression of up to 30%, preferably up to 20%. By radial compression is meant the compression exerted on the sealing ring along the annular plane. According to the invention an O-ring seal with a gas permeation of 100 to 500 $N*cm^3*mm/(m^2*h*bar)$ and a cord thickness of 0.3 to 3 mm, preferably 0.5 to 2 mm, more preferably 0.75 to 1.5 mm, is proposed which seals off a piston reciprocating along its longitudinal axis in a guide tube and is held in a groove, the seal having a radial and possibly axial compression of up to 30%, preferably up to 20% and having a groove filling level of 90 to 100%. By a groove filling level of 90% is meant that 90% of the volume of the groove is filled by the seal.

The preferred sealing material is silicon.

The pump according to the invention can be operated mechanically or electrically. Details may be found in the prior art. These embodiments may be controlled electronically, preferably using a microchip.

The piston may be operated for example by coupling to a piezoelectric element. This coupling may be direct, via one or more lever arms or a diaphragm. Preferably, the piston is moved directly by the piezoelectric element. The piezoelectric element itself is actuated by the microchip, for example, in such a case.

The piston may also be operated by means of a spring, e.g. a helical spring, which is mechanically or electrically biased and connected to the piston via a flange. Details may be found from the prior art relating to medical devices, particularly the fields of transdermal therapeutic systems, atomisers, propellant-free inhalers, needleless injectors, etc.

Basically, any physiologically acceptable solvents or mixtures of solvents in which the active substance dissolves sufficiently may be used with the medical devices according to the invention and the pumping system described. By "sufficiently" is meant concentrations of active substance in the solvent such as to allow a therapeutically active quantity of active substance to be administered.

Preferred solvents are water and pharmacologically acceptable alcohols such as ethanol. If it should prove necessary, solubilisers and complexing agents may be used to increase the solubility of the active substance in the solvent. Sensitive or unstable active substances may contain additives to extend their shelf life.

The medical device according to the invention contains a reservoir for storing the active substance solution, a liquid-conveying connection between the reservoir and the pump according to the invention, and a liquid-conveying connection to at least one device which delivers the liquid. The latter may be a nozzle, a micro-pin or a microcutter along which the liquid is passed, a canula or an outlet. Microcutters and micro-pins are described in detail in EP 0840634 and in FIG. 6 therein, while nozzle systems may be inferred from EP 1017469. Such nozzle systems may comprise a single nozzle opening or a plurality of nozzle openings. Such a nozzle may be a body with at least two or more continuous bores extending parallel to one another or inclined relative to one another. In the case of bores which are inclined relative to one another the end with the acute angle is the nozzle outlet end and the other end is the nozzle inlet end.

The devices according to the invention are preferably used to measure out small volumes of liquids, e.g. less than 1 ml or even less than 100 microliters, from a storage system through the pumping and/or measuring system into a pumping chamber from where the liquid is conveyed to the device which delivers it. Such systems comprise, for example, transcorneal therapeutic systems (TTS, "patch" systems), atomisers, particularly pumping systems in nasal sprays, inhalers, eye washes, infusion systems, needleless injectors, etc, provided that they measure out and deliver propellant-free liquids in order to administer them to a patient.

Transcorneal therapeutic systems continuously or discontinuously transfer pharmaceutical formulations from a storage container through the skin into a patient. Thus the pumping system according to the invention may be incorporated, for example, in a TTS as described in EP 0840634, to which reference is hereby expressly made. A system of this kind may consist of a storage system, into which the pump piston of the pumping system according to the invention projects, which is preferably in the form of a hollow piston with an integrated non-return valve. The hollow piston opens into the measuring chamber from which a release system leads into one or more pin-like projections. The pin-like projection or projections is or are also hollow and constructed so as to penetrate into the corneum of the patient when the patch system is attached to the patient's skin ready for use, so that the liquid can be pumped in. In a system of this kind the release system which consists of at least one tube preferably has one or more non-return valves.

DESCRIPTION OF THE FIGURES

In a piston pump for metering very small volumes a quantity of liquid of about 15 microliter has to be conveyed very precisely in a single piston stroke. This must also be the case even when the device is actuated for the first time after a period of idleness. To ensure this, no air must enter the pump during the period of idleness as otherwise the metering can longer be carried out with the desired precision.

Figure 1:
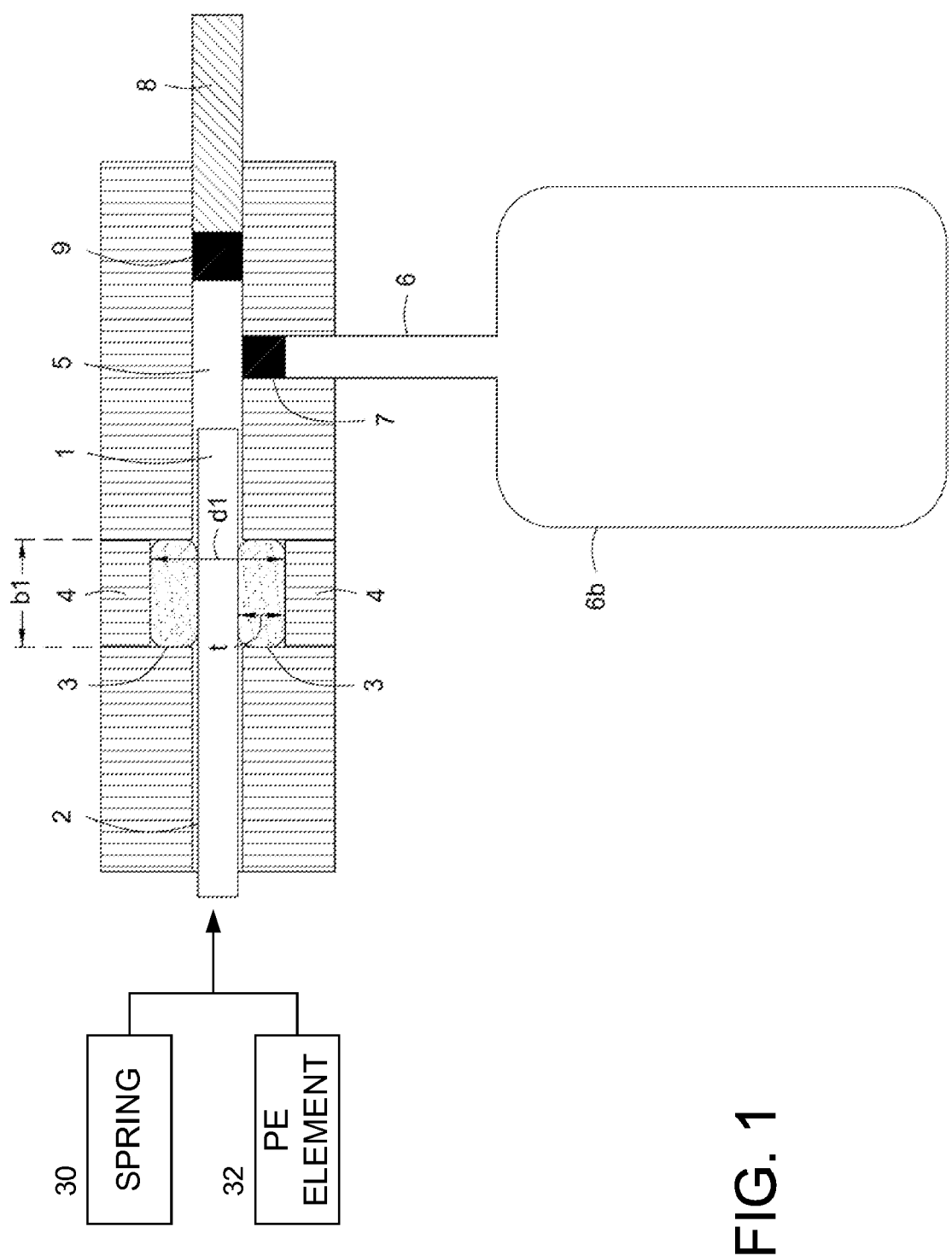
FIG. 1 shows a pumping system of this kind with a piston 1 having a diameter of 1.5 mm. The piston opens into the pumping chamber 5. The piston is guided within a guide tube 2 and sealed off by means of an O-ring seal 3 in a groove 4. The O-ring has a cord thickness of d1=1.1 mm, for example, and a radial compression of about 20% is set. This results in a groove depth of t =0.9 mm. In order to set the groove filling level a groove width of $b_1$=1.1 mm is selected so as to achieve a groove filling level of 95%

For chemical reasons a silicon elastomer is used as the sealing material.

The piston travels into the pumping and measuring chamber 5. Opening into the chamber is a feed tube 6 with a non-return valve 7 through which liquid is sucked in.

A release tube 8 with a non-return valve 9 draws liquid out of the chamber. The storage chamber is generally designed 6b.

The piston may also be operated by means of a spring 30, e.g. a helical spring, which is mechanically or electrically biased and connected to the piston via a flange. Details may be found from the prior art relating to medical devices, particularly the fields of transdermal therapeutic systems, atomisers, propellant-free inhalers, needleless injectors, etc.

The piston may be operated for example by coupling to a piezoelectric element 32. This coupling may be direct, via one or more lever arms or a diaphragm. Preferably, the piston is moved directly by the piezoelectric element 32. The piezoelectric element 32 itself is actuated by a microchip, for example, in such a case.

Figure 2:
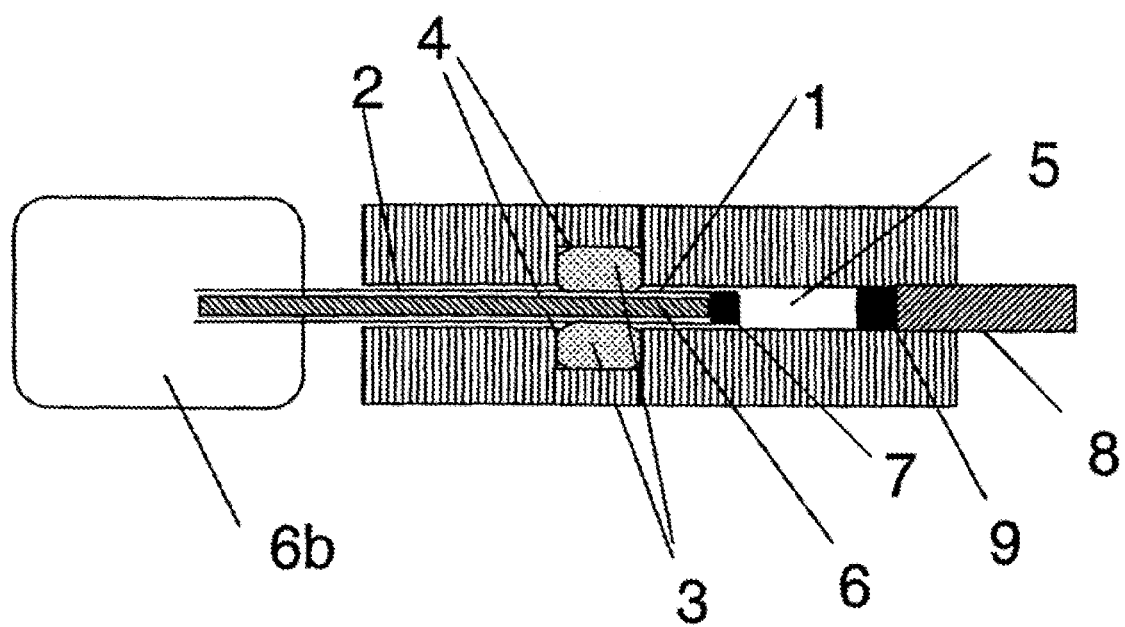

FIG. 2 shows the system according to FIG. 1 in which the feed tube 6 is integrated in the piston 1.

Figure 3:
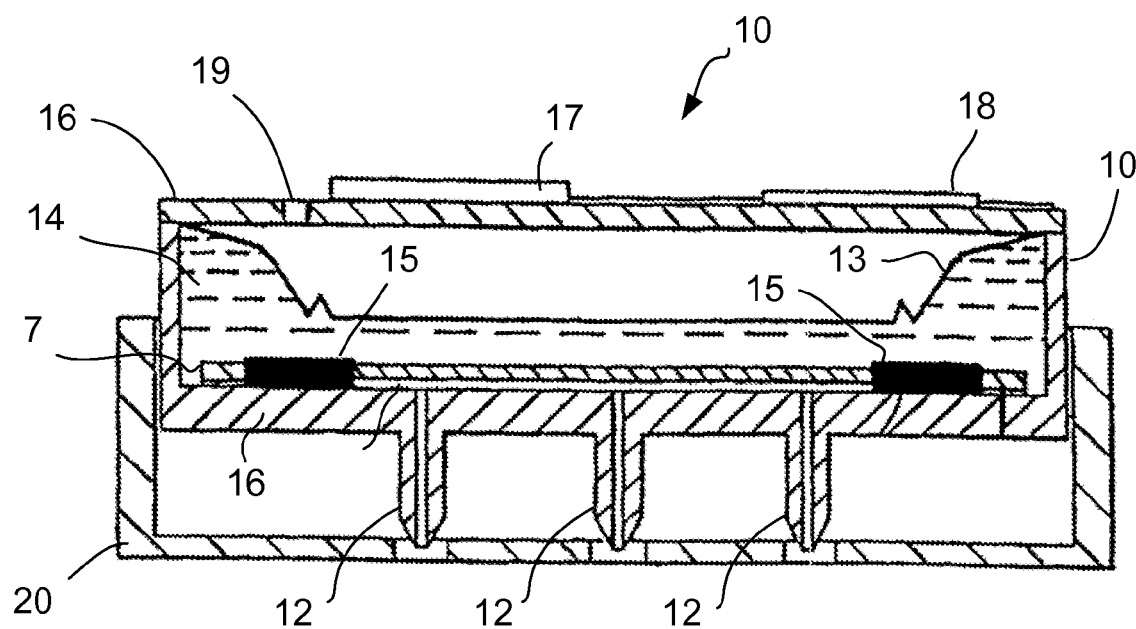

FIG. 3 shows a transdermal therapeutic system with the pump according to the invention. The drawing shows a section through a transcorneal system 10 with an active substance reservoir sealed off at the top by a bellows 13. In the active substance reservoir is the active substance solution 14 which is conveyed outwards at the lower end of the active substance reservoir through a system 15 according to FIG. 2 to the micro-pins with capillary openings 12 provided on the underside of the housing. The side parts 16 of the housing and the underside of the housing together with the micro-pins form a structural unit, preferably of thermoplastic plastics. The lid of the housing contains the energy supply in the form of a battery 17 for operating the pumping system and an electronic control 18, e.g. a microchip. Venting means 19 allow the bellows to adapt to the decreased volume as active substance solution is delivered through the micro-pins. Before the transcorneal system is used the micro-pins are protected by a pin protector 20, for example in the form of a cap.

Figure 4:
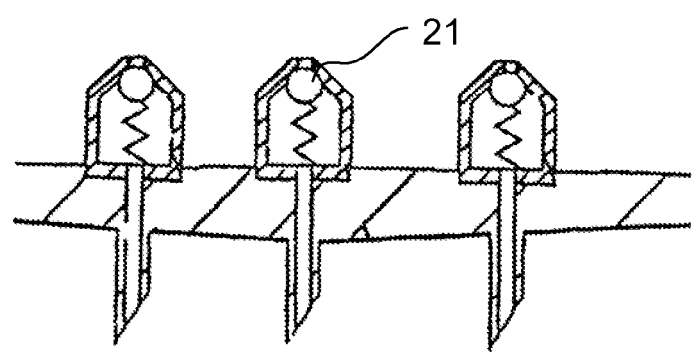

If desired, the micro-pins may contain microvalves 21 as shown in FIG. 4.

What is claimed is:

1. A piston pumping system comprising a piston guided within a guide tube and capable of performing a stroke movement along its longitudinal axis, opening into a pumping chamber, the pumping chamber being connected via a liquid-conveying connection with valve to a storage vessel and from the pumping chamber a liquid conveying connection leads to a device for delivering the liquid, wherein within the guide tube is formed an O-ring seal held by a groove which seals off the piston, has a gas permeation coefficient of 100 to 500 $N*cm^3*mm/(m^2*h*bar)$ for nitrogen ($N_2$) and a radial compression of less than 30% and the seal fills the groove with a groove filling level of more than 90%.

2. A piston pumping system according to claim 1, wherein the groove filling level is more than 95%.

3. A piston pumping system according to claim 1, wherein the valve is a non-return valve.

4. A piston pumping system according to claim 1, wherein a non-return valve is formed in the connection to a device for delivering the liquid.

5. A piston pumping system according to claim 1, wherein the piston has a diameter of 0.25 to 4 mm.

6. A piston pumping system according to claim 1, wherein the piston has a length of 5 mm to 10 cm.

7. A piston pumping system according to claim 1, wherein the stroke movement of the piston along its longitudinal axis covers a length from 1 mm to 5 cm.

8. A piston pumping system according to claim 1, wherein the O-ring seal consists of silicon.

9. A piston pumping system according to claim 1, wherein the piston is a hollow piston in which the liquid-conveying connection with a valve, which connects the pumping chamber to a storage vessel, is integrated.

10. A piston pumping system according to claim 1, wherein the movement of the piston is mechanically controlled.

11. A piston pumping system according to claim 10, wherein the piston is moved by a helical spring.

12. A piston pumping system according to claim 1, wherein the movement of the piston is electronically controlled.

13. A piston pumping system according to claim 12, wherein the piston is controlled by a microchip.

14. A piston pumping system according to claim 12, wherein the piston is moved by a piezoelectric element.

15. A piston pumping system according to claim 1, wherein the pump volume is from 1 microliter to 1 ml.

16. A piston pumping system according to claim 1, wherein the device for delivering the liquid is at least one nozzle, at least one micro-pin or at least one microcutter along which the liquid is guided, at least one canula and/or at least one outlet.

17. A piston pumping system according to claim 1, wherein the cord thickness of the O-ring is from 0.3 to 3 mm.

* * * * *